United States Patent [19]

Nara et al.

[11] Patent Number: 4,686,284
[45] Date of Patent: Aug. 11, 1987

[54] PRODUCTION OF MONOMERIC HUMAN γ-INTERFERON

[75] Inventors: Kiyoshi Nara, Kyoto; Susumu Honda, Takatsuki, both of Japan

[73] Assignee: Takeda Chemical Industries, Ltd., Osaka, Japan

[21] Appl. No.: 654,789

[22] Filed: Sep. 26, 1984

[30] Foreign Application Priority Data

Oct. 4, 1983 [JP] Japan .................................. 58-186383

[51] Int. Cl.$^4$ ...................... C07K 15/26; A61K 45/02
[52] U.S. Cl. ..................................... 530/351; 424/85; 435/811
[58] Field of Search ................... 424/85; 435/68, 811, 435/172.3; 260/112 R, 112.5 R; 530/351

[56] References Cited

U.S. PATENT DOCUMENTS

| | | | |
|---|---|---|---|
| 3,981,991 | 9/1976 | Stewart et al. | 424/85 |
| 4,100,150 | 7/1978 | Cartwright | 424/85 |
| 4,278,661 | 7/1981 | Knight, Jr. | 435/811 |
| 4,432,895 | 2/1984 | Tarnowski | 424/85 |
| 4,476,049 | 10/1984 | Kung | 424/85 |

FOREIGN PATENT DOCUMENTS

| | | |
|---|---|---|
| 0077670 | 4/1983 | European Pat. Off. . |
| 0080879 | 6/1983 | European Pat. Off. . |
| 89692 | 9/1983 | European Pat. Off. . |

OTHER PUBLICATIONS

Giovanni Di Sabato; Purification and Initial Characterization of Rat Interleukin 2; Proceedings of the National Academy of Sciences; Jan. 1982, vol. 79, No. 1; pp. 3020–3023.

*Primary Examiner*—Blondel Hazel
*Attorney, Agent, or Firm*—David G. Conlin; Linda M. Buckley

[57] ABSTRACT

Monomeric human γ-interferon is efficiently produced by subjecting crude human γ-interferon to gel filtration in the presence of a reducing sulfur compound and a protein-denaturing agent.

15 Claims, 2 Drawing Figures

Figure 1

```
  1
Cys Tyr Cys Gln Asp Pro Tyr Val Lys Glu
                                     20
Ala Glu Asn Leu Lys Lys Tyr Phe Asn Ala

Gly His Ser Asp Val Ala Asp Asn Gly Thr
                                     40
Leu Phe Leu Gly Ile Leu Lys Asn Trp Lys

Glu Glu Ser Asp Arg Lys Ile Met Gln Ser
                                     60
Gln Ile Val Ser Phe Tyr Phe Lys Leu Phe

Lys Asn Phe Lys Asp Asp Gln Ser Ile Gln
                                     80
Lys Ser Val Glu Thr Ile Lys Glu Asp Met

Asn Val Lys Phe Phe Asn Ser Asn Lys Lys
                                    100
Lys Arg Asp Asp Phe Glu Lys Leu Thr Asn

Tyr Ser Val Thr Asp Leu Asn Val Gln Arg
                                    120
Lys Ala Ile His Glu Leu Ile Gln Val Met

Ala Glu Leu Ser Pro Ala Ala Lys Thr Gly
                                    140
Lys Arg Lys Arg Ser Gln Met Leu Phe Arg
                        146
Gly Arg Arg Ala Ser Gln
```

PRODUCTION OF MONOMERIC HUMAN γ-INTERFERON

This invention relates to a method for producing monomeric human γ-interferon.

Interferons (hereinafter sometimes abbreviated as IFNs) are proteins produced by higher animal cells upon induction by stimulation by viruses, nucleic acids, etc., and have antiviral, antitumor and other activities.

Today, interferons are generally classified into three types differing in characteristic properties, namely o, β and γ types.

Studies on α type interferon (hereinafter abbreviated as IFN-α) and β type interferon (hereinafter abbreviated as IFN-β) have considerably advanced, improved methods of purification thereof have been developed and properties thereof have become known to a considerable extent.

γ type interferon (hereinafter sometimes abbreviated as IFN-γ) is produced by immunocompetent cells under circumstances such that blast transformation of lymphocytes or lymphokine production can take place, and accordingly it is also called immune interferon. IFN-γ is said to have higher antiproliferative or antitumor activity as compared with IFN-α and IFN-β and therefore more advantageous from the clinical application standpoint. However, due to various limitations, such as the requirement of fresh lymphocytes for the production thereof, any efficient production systems have not been established yet. It has been suggested that, in different experiment systems, different cell species can possibly produce different molecular species of IFN-γ in many aspects, their structures and properties still remain unknown.

The present inventors were engaged in research and development aiming at developing a technology for purifying human IFN-γ produced by utilizing a genetic engineering technique. In the course of a relevant study, they found that IFN-γ has a strong tendency to polymerize and this results in a very poor yield of monomeric human IFN-γ.

While there are only a few papers dealing with the physical and chemical characteristics of human IFN-γ, it is known that it can have polymeric forms. However, how to convert the polymeric forms to the monomeric form or how to prevent the conversion from the monomeric form to the polymeric forms is not previously known.

In accordance with the present invention, there is provided a method for producing monomeric human IFN-γ which comprises subjecting crude human IFN-γ to gel filtration in the presence of a reducing sulfur compound and a protein-denaturing agent.

Said crude human IFN-γ to be purified by the method of the invention may be any human IFN-γ-containing material. For instance, there may be used a crude product obtained by concentration of naturally occurring human IFN-γ, i.e. natural IFN-γ (nIFN-γ) or a human IFN-γ-containing material produced by cultivating a human IFN-γ-producing microorganism obtained in turn by the gene manipulation technology [cf. European Patent Publication No. 0 089 676; Nucleic Acids Research, 10, 2,487–2,501 (1982); Nature, 295, 503–508 (1982); Nucleic Acids Research, 10, 3605–3615 (1982)], i.e. recombinant IFN-γ (rIFN-γ). More concretely, the above-mentioned rIFN-γ includes the polypeptide (I), consisting of 146 amino acids, for example, of the sequence shown in FIG. 1 and its various fragments, such as N terminal portion-deficient species, i.e. lacking not more than 2 amino acids of the N terminal part of polypeptide (I) and C terminal portion-deficient species which are cleaved at a site not earlier than the 131st amino acid residue of polypeptide (I), e.g. a protein which is cleaved between the 131st and 132nd amino acid residue and has Lys at the C terminal end.

From a practical standpoint, an IFN-γ-active fraction obtained by extracting the cells of the above-mentioned IFN-γ-producing microorganism following cultivation thereof or an active fraction obtained from said extract by fractionation with ammonium sulfate, by elution from an antibody column or by ion exchange elution, is used. However, since a greater amount of contaminant proteins uneconomically requires a larger amount of reducing sulfur compound, the use of an antibody column or ion exchange column eluate is generally preferred. In such crude material, IFN-γ may occur in polymerized forms.

The reducing sulfur compound includes organic sulfur compounds such as cysteine, N-acetylcysteine, N-acetylhomocysteine, glutathione (reduced form), thioethanolamine, monothioglycerol, dithiothreitol, thioalkanes having 1–7 carbon atoms and formaldehyde sodium sulfoxilate dihydrate as well as inorganic sulfur-containing compounds such as metabisulfites (sodium salt, potassium salt).

The protein-denaturing agent includes, among others, guanidine salts (hydrochloride, sulfate), urea and thiocyanates (sodium salt, potassium salt).

The gel to be used in said gel filtration can be selected optionally from among commercially available gels. Preferred are granular gels such as dextran, polyacrylamide and agarose. In treating crude human IFN-γ produced by a gene manipulation technique, for instance, the use of a gel capable of effecting fractionation in the molecular weight range of about 1,000–80,000 is favorable in view of the efficiency of separation of contaminant proteins therefrom. More specifically, Sephadex G50 and G75 (cross-linked dextran gel with epichlorohydrin) and Sephacryl S-200 (cross-linked dextran gen with N, N'-bisacrylamide) which are sold by pharmacia Ltd., Biogel P-10, P-30 and P-60 (polyacrylamide gel) sold by Bio-Rad Ltd. and Sepharose 6B (agarose gel) sold by Pharmacia Ltd. are especially preferred.

The gel is used generally in an amount of 5–100 times (weight by weight), preferably 10–30 times (weight by weight), the amount of the sample to be treated.

The gel filtration is suitably carried out by the conventional column method.

Thus, crude human IFN-γ is dissolved in a buffer, for instance, and the aqueous solution is treated on a gel column equilibrated in advance with a developing solvent. Elution is conducted with the developing solvent. The preferred rate of elution, which depends on the purity of the sample and the kind and amount of the gel, is generally within the range of 0.1–10 in terms of SV (space velocity), more preferably 0.5–3. The eluate is fractionated in the conventional manner.

Human IFN-γ-containing fractions can be easily detected by the conventional method, for example by examining an elution curve based on O.D. 280 nm absorption data, among others.

The reducing sulfur compound and protein-denaturing agent may be added to the human IFN-γ in any step of the above gel filtration process. The reducing sulfur compound and protein-denaturing agent are preferably added to the aqueous human IFN-γ solution to be subjected to gel filtration and the developing solvent.

In cases where a protein-denaturing agent is used in a pretreatment step, such as extraction or antibody column treatment, the aqueous solution to be treated on the gel column can be used without further addition of such agent.

The aqueous solution to be treated and the developing solvent preferably have a pH of 5.0-8.0, especially a pH around neutrality, and preferably contain the reducing sulfur compound in a concentration of 1-100 mM, preferably 5-20 mM and the protein-denaturing agent in a concentration of 0.1-7 M, especially 1-2 M. As a buffer for the aqueous solution and developing solvent mentioned above, Trishydrochloride, acetate, phosphate and borate buffers are may be used, and preferably phosphate buffer.

The reducing sulfur compound and protein-denaturing agent contained in the thus-obtained eluate which contains purified human IFN-γ can be removed as necessary. Gel filtration is preferably conducted to the separation of such low molecular weight compounds and human IFN-γ which is a high molecular weight compound.

Such gel filtration can be carried out in the same manner as the gel filtration for monomerization mentioned above, with the use of a gel suited for removing low molecular weight compounds, for example Sephadex 25.

In case the removal of the reducing sulfur compound is to be secured, the eluate can be subjected to ultrafiltration by the conventional procedure.

In the process of separating these low molecular weight compounds from human IFN-γ, human serum albumin, for instance, may be added so as to stabilize human IFN-γ.

The thus-purified monomeric human IFN-γ can be lyophilized to a powder form as necessary.

The monomeric human IFN-γ produced in accordance with the invention can be used for the same purposes and in the same modes of use as in the case of conventional IFN-γ products. Since it is relatively free of contaminant proteins and pyrogen as compared with the conventional products, it can be used more safely as a bulk substance for producing injectable preparations, among others.

The monomeric human IFN-γ produced in accordance with the invention shows antiviral, antitumor, antiproliferative and immunopotentiating activities and can be administered in the same manner as previously known IFN-γ.

The IFN activity as described herein in terms of antiviral activity in U/ml (units/ml) was determined in the following manner. An international standard IFN-α for which the unit has been established and leukocyte-derived crude IFN-γ were assayed in the test for estimating the inhibitory effect against cell degeneration caused in a human amnion-derived FL cell line by VSV (vesicular stomatitis virus), the titer of the lymphocyte-derived IFN-γ was determined by comparison of the titers found, and said IFN-γ was used as a laboratory standard IFN-γ. In calculating the titer of IFN-γ in a material, this laboratory standard IFN-γ was always used in parallel in the above-mentioned assay in the WISH-VSV system and the titer calculation was performed based on the titer ratio.

In the present specification and claims, mM and M mean millimolar concentration and molar concentration, respectively.

BRIEF DESCRIPTION OF THE DRAWINGS

FIG. 1 illustrates the amino acid sequence of polypeptide (I) as an example of rIFN-γ.

Figure 2:
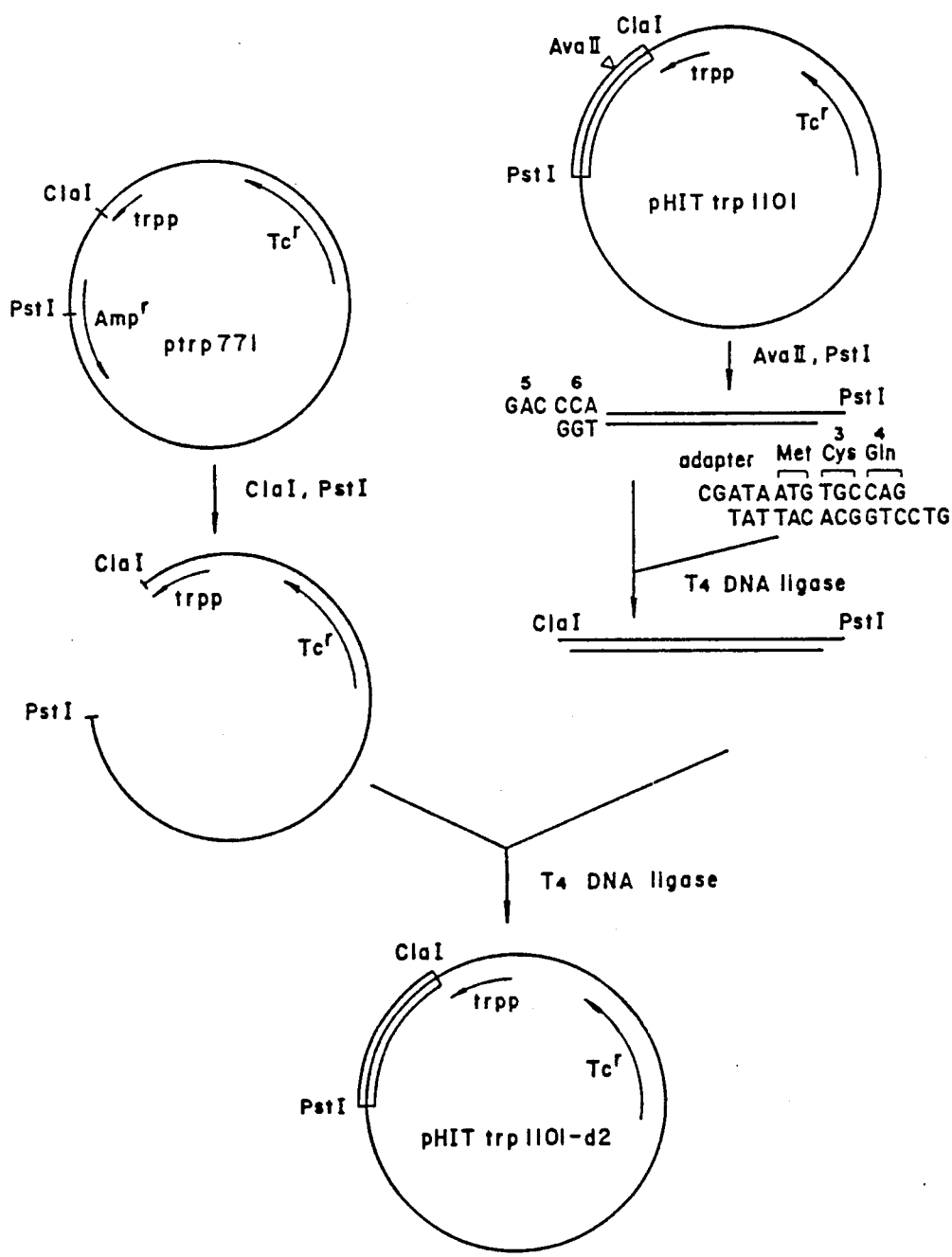
FIG. 2 illustrates the contruction scheme for plasmid pHIThp1101-d2 described in Reference Example 2 (i).

The following examples and reference example illustrate the present invention in more detail but are by no means limitative of the present invention.

The antibody column Ab (Mo γ-2-11.1) as described in the examples was prepared by the method disclosed in European Patent Publication No. 0 103 898 which claims also International Application PCT/JP83/00174 (filed May 31, 1983).

EXAMPLE 1

(i) To 100 g of the frozen cells obtained in Reference Example 1 was added 300 ml of 100 mM Tris hydrochloride buffer (pH 7.0) containing 7 M guanidine hydrochloride and 2 mM phenylmethylsulfonyl fluoride. The mixture was stirred at 4° C. for 1 hour and centrifuged (17,000 rpm/30 minutes). The clear and transparent supernatant thus obtained was diluted 70-fold with a buffer comprising 137 mM sodium chloride, 2.7 mM potassium chloride, 8 mM disodium hydrogen phosphate and 1.47 mM monopotassium dihydrogen phosphate (hereinafter abbreviated as "PBS"). The resultant precipitate was removed using a Sharples centrifuge (10,000 rpm) and the supernatant obtained (22 liters) was concentrated to a volume of 1.5 liters using a Pericon membrane filter (Millipore Corp.; molecular weight cut-off: 10,000). The concentrate was allowed to stand at 4° C. overnight and the resultant precipitates were removed by further centrifugation (10,000 rpm/30 minutes). A preliminarily packed antibody column [Ab (Mo γ2-11.1); 5×3 cm] was loaded with the supernatant obtained, at a flow rate of 1,000 ml/hour. Through the column, there were passed washing solutions, namely 500 ml of PBS, 1,000 ml of 10 mM phosphate buffer (pH 7.0) containing 1 M sodium chloride and 0.1% of Tween 20, 500 ml of PBS and 500 ml of 20 mM phosphate buffer (pH 7.0) containing 0.5 M guanidine hydrochloride, in that order. Thereafter, elution was carried out with 20 mM phosphate buffer (pH 7.0) containing 2 M guanidine hydrochloride to give 62 ml of antivirally active eluate fractions.

(ii) A column (5.0×60.0 cm) of Sephacryl S-200 (Pharmacia) preliminarily equilibrated with 25 mM acetate buffer (pH 5.0) containing 1 mM ethylenediaminetetraacetate, 150 mM sodium chloride, 10 mM cysteine hydrochloride and 2 M guanidine hydrochloride was loaded with 62 ml of the IFN-γ eluate obtained in Example 1-(i), followed by elution with the same buffer, giving 83 ml of monomer eluate fractions. The thus-obtained fractions showed convergence to the monomeric form also in slab electrophoresis using sodium dodecyl sulfate (hereinafter referred to as SDS-PAGE) (apparent molecular weight: about 18,000). Thus molecular sieve treatment gave 3.7 mg of IFN-γ having a specific activity of $1.5 \times 10^7$ U/mg of protein. In a control run in which the IFN-γ obtained by the procedure of Example 1-(i) was treated in the same manner as in Example 1-(ii) except that the developing solvent for gel filtration was free of 10 mM cysteine hydrochloride, dimer and oligomer fractions accounted for about 90% of the whole eluate and monomer fractions only for about 10%. This result thus evidenced the effect of the coexisting cysteine hydrochloride and guanidine hydrochloride to cause convergence to the monomeric form.

(iii) A Sephadex G-25 column (5.0×60.0 cm) equilibrated in advance with a 25 mM acetate buffer (pH 6.0) containing 10 mM cysteine hydrochloride, 150 mM sodium chloride and 0.01% Tween 20 was loaded with 83 ml of the IFN-γ-containing eluate obtained in Example 1-(ii), followed by elution with the same buffer. The thus-obtained IFN-γ-containing eluate fractions (90 ml; 2.7 mg) was free of quanidine hydrochloride had a specific activity of $1.7 \times 10^7$ U/mg of protein.

(iv) To 90 ml of the IFN-γ-containing eluate obtained in Example 1 (iii), there was added 450 mg of human serum albumin. After dissolution, the solution was concentrated by ultrafiltration using a Diaflo PM-10 membrane (Amicon's ultrafiltration membrane) to 60 ml. A Sephadex G-75 column (5×60 cm) equilibrated in advance with a 25 mM phosphate buffer (pH 7.0) containing 150 mM sodium chloride was loaded with the concentrate, followed by development and elution with the same buffer to give IFN-γ-containing fractions. This procedure removed the remaining portion of cysteine from the IFN-γ-containing eluate obtained in Example 1-(iii) and there was obtained 33 ml (2.2 mg) of an IFN-γ solution containing human serum albumin instead and having a specific activity of $1.5 \times 10^7$ U/mg of protein.

EXAMPLE 2

Glutathione (reduced form) was added, in an amount giving a concentration of 10 mM, to the antibody column eluate obtained by the same procedure as Example 1-(i), to give a monomer-rich crude IFN-γ solution (63 ml; 11 mg) having a specific activity of $3.0 \times 10^6$ U/mg of protein. Then, this crude IFN-γ solution was treated in the same manner as in Example 1-(ii) except that the buffer for gel filtration contained 10 mM glutathione (reduced form) in place of cysteine. The monomer eluate fractions thus collected (85 ml) showed convergence to the monomer form also in SDS-PAGE (apparent molecular weight: about 18,000). Addition of 425 mg of human serum albumin to the eluate (85 ml) followed by gel filtration gave an IFN-γ solution (90 ml) freed of the guanidine hydrochloride and having a specific activity of $1.8 \times 10^7$ U/mg of protein.

EXAMPLE 3

(i) Frozen cells (5.9 g) obtained in Reference Example 2(ii) were suspended in 18 ml of 0.1 M Tris·HCl buffer (pH 7.0) containing 7 M guanidine.HCl and 2 mM phenylmethylsulfonyl fluoride. The mixture was stirred at 4° C. for 1 hr and then centrifuged at $10,000 \times g$ for 30 min. The resulting supernatant (20 ml) was diluted with 260 ml of the buffer containing 137 mM NaCl, 2.7 mM KCl, 8.1 mM $Na_2HPO_4$ and 1.5 mM $KH_2PO_4$ (pH 7.4) (abbreviated as PBS) and then applied to a monoclonal antibody (Moγ2-11.1) column (bed volume, 12 ml) at a flow rate of 1 ml/min. The column was washed with 60 ml of 20 mM sodium phosphate buffer (pH 7.0) containing 0.5 M guanidine·HCl and then the polypeptide was eluated with 36 ml of 20 mM sodium phosphate buffer (pH 7.0) containing 2 M guanidine·HCl to obtain 20 ml of a fraction having the antiviral activity.

The fraction (20 ml) was applied to a Sephacryl S-200 (Pharmacia Fine Chemicals) column (2.6×94 cm; bed volume, 500 ml) which was equilibrated with 25 mM ammonium acetate buffer (pH 6.0) containing 2 M guanidine·HCl, 0.15 M NaCl, 1 mM ethylenediamine tetraacetate and 10 mM cysteine and eluted with the same buffer to obtain 37 ml of a fraction having antiviral activity.

The amount of the polypeptide thus obtained was 5.9 mg and the specific activity was $1.0 \times 10^7$ U/mg. Analysis of the preparation by sodium dodecylsulfatepolyacrylamide gel electrophoresis according to the method of Laemmli [Nature, 227 680–685 (1970)] showed that the molecular weight of the polypeptide was about 18,000. Under non-reducing conditions, only a slight protein band was observed at the position which corresponds to the dimers molecular weight.

REFERENCE EXAMPLE 1

The strain RR1 (pRK248cIts, pRC231/IFI-900) carrying the human IFN-γ expression gene as described in Example 8 in European Patent Publication No. 0 089 676 was cultivated in M9-glucose medium at 30° C. until the cell concentration reached 3 to $4 \times 10^8$ cells/ml. Glucose and casamino acids were added in concentrations of 1.0% and 0.5%, respectively. After an hour of induction at 42° C., the culture was centrifuged and the cells thus obtained were frozen and stored. The rIFN-γ contained therein has the amino acid sequence shown in FIG. 1.

REFERENCE EXAMPLE 2

(i) An IFN-γ expression plasmid pHITtrp1101 (refer to Example 2(iii) of European Patent Publication No. 0 110 044) was digested with the restriction enzymes AvaII and PstI, and then an AvaII-PstI 1kbDNA fragment containing the structural gene of IFN-γ was isolated. To the stricky end of AvaII of the thus obtained DNA fragment, an oligonucleotide adapter containing the protein synthesis start codon

CGATAAT.GTGCCAG

TATTACACGGTCCTG which was chemically synthesized by the triester method was ligated using T4DNA ligase.

To the downstream of trp promoter of the DNA fragment obtained by cutting the plasmid ptrp771 (refer to Example 2(ii) of the above-mentioned publication) with restriction enzymes ClaI and PstI, was inserted IFN-γ structural gene connected with the above-mentioned adapter to construct the expression plasmid pHITtrp1101-d2 (FIG. 2).

*Escherichia coli.* 294 was transformed with the thus obtained plasmid pHITtrp1101-d2 by the method of Cohen et al. [Proc. Natl. Acad. Sci. USA., 69, 2110(1972)]to obtain the transformant *Escherichia coli.* 294/pHITtrp1101-d2 which was deposited at Institute for Fermentation, Osaka as IFO-14350.

(ii) *E. coli.* 294/pHITtrp1101-d2 was incubated in M9 medium containing 8 μg/ml tetracycline, 0.4% casamino acid and 1% glucose at 37° C. When the growth reached KU220, 3β-indolyl acrylic acid (IAA) was added at a concentration of 25 μg/ml and the mixture was further incubated for 4 hours. After the incubation, the cells were collected by the centrifugation. The rIFN-γ contained therein has the amino sequence of No. 3 to No. 146 in FIG. 1.

What is claimed is:

1. A method for producing monomeric human γ-interferon, which comprises subjecting crude human γ-interferon to gel filtration in the presence of a reducing sulfur compound and a protein-denaturing agent.

2. A method according to claim 1, wherein the reducing sulfur compound is an organic sulfur compound.

3. A method according to claim 2, wherein the organic sulfur compound is a member selected from a group consisting of cysteine, N-acetylcysteine, N-acetylhomocysteine, glutathione (reduced form), thioethanolamine, monothioglycerol, dithiothreitol, thioalkane having 1-7 carbon atoms and formaldehyde sodium sulfoxilate dihydrate.

4. A method according to claim 3, wherein the organic sulfur compound is glutathione (reduced form).

5. A method according to claim 1, wherein the protein-denaturing agent is a member selected from a group consisting of guanidine salt, urea and thiocyanate.

6. A method according to claim 5, wherein the protein-denaturing agent is guanidine salt.

7. A method according to claim 1, wherein the crude human γ-interferon is a recombinant human γ-interferon.

8. A method according to claim 1, wherein the crude human γ-interferon is an eluate of an antibody column loaded with an extract containing human γ-interferon.

9. A method according to claim 1, wherein the gel is a member selected from a group consisting of dextran, polyacrylamide and agarose.

10. A method according to claim 9, wherein the gel is dextran.

11. A method according to claim 1, wherein the gel filtration is conducted by loading crude human γ-interferon dissolved in a buffer solution containing a reducing sulfur compound and a protein-denaturing agent on a column packed with granular gel and then eluting the γ-interferon with the same buffer solution.

12. A method according to claim 11, wherein the buffer solution contains the reducing sulfur compound and the protein-denaturing agent in a concentration of about 1 to 100 mM and about 0.1 to 7 M, respectively.

13. A method according to claim 11, wherein the buffer solution is of about pH 5.0 to 8.0.

14. A method according to claim 11, wherein the elution is conducted at a space velocity of about 0.1 to 10.

15. A method according to claim 1, further comprising a gel filtration step using a gel suited for removing low molecular weight compounds to obtain monomeric human γ-interferon free from reducing sulfur compound and protein-denaturing agent.

* * * * *